United States Patent
Agrawal et al.

(10) Patent No.: US 8,003,394 B2
(45) Date of Patent: Aug. 23, 2011

(54) METHODS FOR METAL ASSAYS USING OPTICAL TECHNIQUES

(75) Inventors: Anoop Agrawal, Tucson, AZ (US); John P. Cronin, Tucson, AZ (US); Lori L. Adams, Tucson, AZ (US); Akshay Agrawal, Tucson, AZ (US); Juan Carlos L. Tonazzi, Tucson, AZ (US)

(73) Assignee: Ajjer LLC, Tucson, AZ (US)

( * ) Notice: Subject to any disclaimer, the term of this patent is extended or adjusted under 35 U.S.C. 154(b) by 55 days.

(21) Appl. No.: 12/533,534

(22) Filed: Jul. 31, 2009

(65) Prior Publication Data
US 2010/0035351 A1    Feb. 11, 2010

Related U.S. Application Data

(60) Provisional application No. 61/085,485, filed on Aug. 1, 2008.

(51) Int. Cl.
*G01N 33/20* (2006.01)

(52) U.S. Cl. ................. 436/79; 436/73; 436/83; 436/84

(58) Field of Classification Search .................... 436/79, 436/73, 83, 84
See application file for complete search history.

(56) References Cited

U.S. PATENT DOCUMENTS
7,129,093 B2   10/2006  McCleskey et al.
2005/0280816 A1*  12/2005  Agrawal et al. ............... 356/317

FOREIGN PATENT DOCUMENTS
WO   WO2008130737   10/2008

OTHER PUBLICATIONS

Determination of a Trace Amount of Beryllium in Water Samples by Graphite Furnace Atomic Absorption Spectrometry after Preconcentration and Separation as a Beryllium-Acetylacetonate Comples on Activated Carbon Tadao Okutani, Yasuhiro Tsurunta, Akio Sakuragawa Analytical Chemistry (1993) 65: 1273-1276.*
U.S. Appl. No. 12/338,724, filed Dec. 18, 2008.
NIOSH 7704, Manual of Analytical Methods (NMAM), 5th Edition.
NIOSH 9110, Manual of Analytical Methods (NMAM), 5th Edition.
ASTM D7202, Standard Test Method for Deterimination of Beryllium in the Workplace Using Field-Based Extraction and Fluorescence Detection. Oct. 2006.
ASTM D7458, Standard Test Method for Determination of Beryllium in Soil, Rock, Sediment, and Fly Ash Using Ammonium Bifluoride Extraction and Fluorescence Detection. Oct. 2008.
NIOSH 7703, Manual of Analytical Methods (NMAM), 5th Edition.
EPA SW846-7196. Jul. 1996.
NIOSH 7700, Manual of Analytical Methods (NMAM), 4th Edition, May 15, 1996.

(Continued)

*Primary Examiner* — Robert J Hill, Jr.
*Assistant Examiner* — Dwan A Gerido
(74) *Attorney, Agent, or Firm* — Lawrence R. Oremland, P.C.

(57) ABSTRACT

An improved optical method for determining metal or a metal compound thereof in a sample with organic impurities. The optical method comprises of solvating the metal in a liquid medium and then mixing this liquid medium with an optical indicator and then measuring the presence of the metal. The improvement lies in removing any organic impurities by the addition of an additive, where the said additive is removed before the optical indicator is added.

13 Claims, 5 Drawing Sheets

OTHER PUBLICATIONS

Matsumiya, H., Hoshino, H., Yotsuyanagi, T., *A novel fluorescence reagent, 10-hydroxybenzo[h]quinoline-7-sulfonate, for selective determination of beryllium(II) ion at pg cm$^{-3}$ levels*, Analyst, vol. 126, pp. 2082-2086 (2001).

Ashley K.; Agrawal, A.; Cronin, J.; Tonazzi, J.; McCleskey, T. M.; Burrell, A. K.; Ehler, D. S., *Ultra-trace determination of beryllium in occupational hygiene samples by ammonium bifluoride extraction and fluorescence detection using hydroxybenzoquinoline sulfonate*, Analytical Chimica Acta, vol. 584, pp. 281-286 (2007).

(Agrawal et al-2) Agrawal, A; Cronin, J.; Agrawal, A; Tonazzi, J.; Ashley, K.; Brisson, M.; Duran, B.; Whitney, G.; Burrell, A.; McCleskey, T.M.; Robbins, J.; White, K., *Extraction and Optical Fluorescence Method for the Measurement of Trace Beryllium in Soils*. Environmental Science and Technology, vol. 42, pp. 2066-2071 (2008).

Agrawal, Anoop; Cronin, John; Adams, Lori; Agrawal, Akshay; Tonazzi, Juan Carlos; *Fluorescence Analysis of Beryllium in Samples Contaminated by Strongly Fluorescent Impurities*, Submitted for publication, Journal of Occupational and Environmental Health (Also presented at Third International Symposium on Beryllium Particulates and Their Detection. Organized by Beryllium Health and Safety Committee (Department of Energy) in Albuquerque, New Mexico, 2008).

\* cited by examiner

METHODS FOR METAL ASSAYS USING OPTICAL TECHNIQUES

RELATED APPLICATION/CLAIM OF PRIORITY

This application is related to and claims priority of provisional application Ser. No. 61/085,485, filed on Aug. 1, 2008, which provisional application is incorporated by reference herein

FIELD OF THE INVENTION

The present invention relates to the detection and quantification of metals by using optical assaying methods. Optical methods such as absorbance and fluorescence are routinely used to determine a variety of metals in a sample matrix, the accuracy of which may be compromised by organic contaminants that interfere with such measurements. This innovation will demonstrate practical methods to overcome interference created by such contaminants.

BACKGROUND OF THE INVENTION

Samples such as solid (bulk), liquid, wipe or an air filter are routinely analyzed for a variety of metallic contaminations. Solid samples such as dust and soil are collected and subjected to a dissolution solution to dissolve the metal or metal compound of interest. Liquid samples such as water may also be analyzed, but in this case dissolution process is not necessary. Wipes are used to determine surface contamination of articles and after wiping a specific amount of area these are subjected to dissolution. Similarly, the air-sampling device comprises of a filter through which a specific volume of air is passed and then the filter is analyzed to determine airborne pollution from the metal of interest after subjecting the filter to dissolution. Most of the quantitative test methods to analyze metals go through a dissolution process and then an analytical procedure to quantify the metal. Some examples of the analytical test methods where dissolution and then an analysis are carried out are NIOSH 7301 (NIOSH is National Institute of Occupational Health and Safety, Atlanta, Ga.), where the material is dissolved using aqua regia, EPA procedure SW-846-3051 (EPA is US Environmental Protection Agency, Washington D.C.) uses microwave digestion with nitric acid. In all these test methods the samples are then analyzed using plasma methods, which typically are not affected by organic impurities. Organic impurities are usually colored, may bind to other molecules that result in color or fluoresce, or can have strong fluorescence signals. In either case all of these may interact with optical detection methods. For those methods that rely on fluorescence, this interference can be two fold, first it can absorb the excitation energy and thus lowering the excitation signal available for the intended fluorophore, and secondly if the impurities emit in the same wavelength region as the intended fluorophore then the analysis may falsely provide elevated levels of metal when only low concentrations of metal are present. Thus in test methods such as NIOSH 7704, 9110 and ASTM D7202 for beryllium analysis by fluorescence such interferences can be severe. Such interferences can also influence optical analytical methods for a variety of other metals, e.g., NIOSH 7703 and EPA SW846-7196 for hexavalent chromium, and NIOSH 7700 for lead. Thus it is desirable to reduce or eliminate interferences due to the organic impurities that will interfere with the results.

Although this invention is applicable to all types of optical analysis for metals, it will be mainly illustrated for analysis of beryllium by fluorescence. Beryllium is a metal that is used in a wide variety of industries including electronics, aerospace, defense, and the US Department of Energy (DOE) complexes. Exposure to beryllium containing particles can lead to a lung disease called Chronic Beryllium Disease (CBD). CBD involves an uncontrolled immune response in the lungs that can lead to deterioration in breathing capacity and ultimately death. It is clear that even in processes where beryllium dust has been controlled to very low levels, cases of disease still persist. In fact, there have been cases of CBD reported in people that have had no obvious direct contact with beryllium operations. Despite the fact that very low exposure levels can lead to CBD, the onset of disease can take decades. Thus it is important that any analytical method provide an accurate assessment of the beryllium or any other metal where this information is used further to make decisions. Optical fluorescence is used to determine beryllium in several standard test methods, e.g., NIOSH 7704, NIOSH 9110, ASTM D7202 and ASTM D7458. These methods follow steps where a sample comprising beryllium or its compound is dissoluted in an aqueous solution of ammonium bifluoride. An aliquot of this solution is added to a buffered solution of an indicator solution comprising 10-hydroxy-benzo[h]quinoline-7-sulfonate (10-HBQS) dye. This solution is measured for fluorescence signal to quantify beryllium. An organic impurity in the sample that may have fluorescence characteristics similar to 10-HBQS can result in a significant error.

One object of the present invention is to demonstrate practical methods of removing the effects of organic impurities from analytes that are analyzed for metal content using optical methods.

Yet another objective of this invention is to demonstrate practical methods of removing the effect of the organic impurities from analytes that are analyzed for beryllium by fluorescence.

SUMMARY OF THE INVENTION

The present invention is to demonstrate practical methods of removing the interfering organic impurities from samples that are analyzed for metal content using optical methods. Typically an optical test to determine a metal presence in a sample comprises of the following steps: admixing a sample suspected of containing metal or a metal compound along with the impurities with a dissolution solution for sufficient time whereby metal or a metal compound within said sample is dissolved, mixing a portion from the admixture with a solution containing a optical indicator capable of binding metal or a metal compound to the optical indicator, and, determining the presence of an amount of metal or a metal compound within the sample by measuring change in optical properties from the optical indicator. This invention describes a practical way of removing the effect of organic impurities which may interfere with the analysis on their own or by interacting with the optical indicator.

DETAILED DESCRIPTION

Beryllium and its oxide are very useful, however their particles are toxic, hence its concentration in the work-place atmosphere, and on the surfaces is highly regulated. Regulations from the DOE (10CFR851) on beryllium dictate a permissible exposure limit of 0.2 $\mu g/m^3$ in air, a housekeeping level of 3 $\mu g/100$ $cm^2$ on a surface, and a release level for materials after beryllium exposure where the surface contamination due to beryllium must not exceed 0.2 $\mu g/100$ $cm^2$. Recently, the American Conference of Governmental Industrial Hygienists (Cincinnati, Ohio) has adopted that the exposure limit for beryllium to be lowered to 0.05 $\mu g/m^3$ which puts pressure on regulatory agencies to follow suit. Optical fluorescence has emerged as an important method for analyzing the presence of beryllium particles with very high sensitivity and low cost. Currently, thousands of surface wipes and air filters are analyzed annually for beryllium. In addition OSHA has detected airborne levels of beryllium at numerous sites within the United States. In some of the sites where past beryllium activity or disposal has taken place, beryllium needs to be cleaned from the soil, down to a level of 131 mg of beryllium in each kg of soil. This effort requires inexpensive methods such as fluorescence to measure beryllium; however, one has to ensure that this is not also contaminated by specific organic materials that may interfere with the analysis. The presence of those organic impurities in samples (along with beryllium) that have spectral characteristics matching the fluorescent indicators used in the test method can compromise the results. This innovation discloses methods to eliminate this interference for beryllium, and in general for any metal analysis that uses optical methods for such characterization.

Although there are several reports of being able to detect beryllium with a fluorescent indicator (see Matsumiya et al), only recently quantitative fluorometric beryllium detection methods have been shown to be effective for the current exposure regulations. A quick, simple and specific approach has now been developed for the detection and quantification of beryllium, see U.S. Pat. No. 7,129,093; Agrawal et al-1 and Agrawal et al-2, which are incorporated herein by reference. This method is specific to beryllium and there are no interferences caused by other elements. Further this method provides a quantitative method of determining beryllium or a compound thereof (including beryllium oxide) in a sample, which has a fast turnaround time and can be made to be readily field portable. Moreover, the method disclosed in U.S. Pat. No. 7,129,093 has been enhanced as demonstrated in published US patent application 20050280816 and in published PCT application WO2008130737 which are also incorporated by reference herein. This fluorescence method is highly accurate and not susceptible to interference from other metals. However, if there are organic materials present in the sample with high intrinsic fluorescence, then they may interfere with accurate determination of beryllium depending on their optical characteristics.

Acids and low pH solutions are often used to dissolve metal and their compounds in a solution and then the solutions are analyzed. Ammonium bifluoride (ABF) aqueous solutions are effective liquid mediums to dissolve beryllium, and its compounds including high fired beryllium oxide. ABF dissolution may also be used for many metals other than beryllium. It has been observed that for high fired beryllium oxide elevated temperature in a range of 80-90° C. is required for effective dissolution. Typical concentrations of ABF solutions used in various standard procedures for beryllium determination are in a range of 1 to 3%, although these concentrations could be changed for specific cases. The organic impurities present in the sample may also be drawn in this medium, which could then interfere with the analysis. If this impurity either absorbs in the excitation wavelength or itself emits in the fluorescence range of interest, it will cause inaccurate results for beryllium concentration determination when fluorescence is used for analysis. One method to remove the organic contaminants is to incorporate additives in the dissolution solution to remove or convert the organics in a non-fluorescent form. Preferred additives that convert are oxidizers or reducing materials. Some examples of additives that remove the organics by absorption or attachment are activated charcoal, acidic alumina and zeolites. Some of the strong reducing materials are zinc powders, ferrocyanide, lithium aluminum hydride, diisobutylaluminum hydride, oxalic acid, hydrazine, sulfite compounds and examples of oxidizers are bleach. Further, examples of bleach are hydrogen peroxide, sodium hypochlorite, calcium hypochlorite, sodium persulfate, sodium perborate, sodium percarbonate, sodium dithionite, chlorine, chloramine to name a few. The wipes for surface sample collection may also be loaded with these additives so as to remove or react with the organic impurities while the sample is collected. Activated charcoal may be purchased from Aldrich Chemical Company (e.g., Darco G60 which is a steam activated grade, acid washed grade, e.g., washed with hydrochloric acid-catalogue number C4386, decolorizing charcoal, etc.). The activated charcoal may be used as a powder or as pellets. However, the additive material selected must be compatible and tested with the solutions and solvents used for a specific analysis.

A preferred method is to add these additives to the dissolution solution. The addition of the additive to the dissolution solution can be done at several stages. The dissolution solution can be premixed with the additive and then it is carried through the dissolution process, or it can be mixed after the dissolution process is over. The advantage in the former is that dissolution solutions with the additives can be sold so that the end-user of the method does not have to deal with addition of components at their facility. Further, these additives should not adversely affect the analysis, i.e., they should not add any additional impurities or bind/remove the element being detected, or lead to any other complications. It is also preferred that this additive be removed from the dissolution solution before adding the optical indicator (or dye component) that leads to fluorescence or absorption. This is because any residual additive can also react or interact with the dye (which are usually organic materials) in the same manner at it interacts with the organic impurity thus skewing the results.

When additives comprise of chemicals such as hydrogen peroxide or bleach, the removal of these additives is pursued by deactivating them, e.g., by heating the dissolution solution for sufficiently long time to ensure the entire residual additive decomposes. These could also be passed through a column that only absorbs residual additive. Alternately, if the additive is granular, then after treating the dissolution solution, it can be removed by a filtration step before mixing it with the optical indicator. Thus if one adds particulate additives (powders, granules, pellets) e.g., activated charcoal or zeolites in a size larger than the filter pore, then these could be removed easily by filtration or another mechanical process such as centrifugation. A typical filter pore size that is used for optical methods to reduce light scattering in analysis is about between 0.1 to 0.5 microns. Thus the size of the additives should preferably be greater than 0.5 microns and more preferably greater than 10 microns or more so that their removal is complete. The particulate additives are preferred as they are easy to remove and compatible with several of the established procedures that use filtration as a step.

The optical indicator solution for beryllium analysis in the above listed standardized procedures uses 10-hydroxybenzo[h]quinoline-7-sulfonate (10-HBQS) as fluorescent indicator. The buffered solution includes a buffer having a pKa in excess of 12.5. A typical buffer that is preferred is an amine buffer such as lysine. A preferred lysine compound is L-lysine monohydrochloride. The solution may also contain aminocarboxylates such as ethylenediaminetetraaceticacid (EDTA), as a chelating agent to bind metals other than beryllium.

The current method of beryllium analysis involves obtaining a sample on a medium (such as on a filter paper by wiping a surface or capturing airborne particles), or a bulk soil sample and then placing the medium into a vial and adding 5 ml to 100 ml of an aqueous ammonium bifluoride solution for dissolution of beryllium captured on the medium. A preferred concentration is one to three percent ammonium bifluoride solution which can dissolve up to 10 mg of either beryllium or beryllium oxide in less than 30 minutes with simple shaking and/or heating to 90° C. A mechanical shaker, oven or a block heater with a timer is preferred for consistency. After cooling, a predetermined quantity of this solution (with dissoluted beryllium sample) is added to a buffered indicator solution after filtering (typically the filter pore size is equal to or less than 2 microns, and a preferred size is 0.45 microns). The fluorescent indicator solution has a buffer, to neutralize the acidic dissolution solution and bind beryllium ions to the fluorescent indicator. When 10-HBQS is used as the fluorescent indicator, fluorescence at 475 nm can be used to quantitatively determine the beryllium.

In the present invention the particulate additive to remove the organic contamination can be added in several ways. One is to add the additive before adding the sample to the dissolution solution, another way is to add additive and the sample at the same time to dissolution solution, or one may add the additive as the last step. In either case dissolution process is carried out while the additive is present or it is extended after the addition of the additive. Dissolution may be a room temperature or an elevated temperature process. The first method is preferred where the dissolution solution with the additive can be prepared in advance and then used as needed. For practical kits, it is important that the dissolution solutions with the additive have a long shelf life (preferably more than one month and more preferably greater than 1 year) so that these may be easily transported and stored for a length of time without deterioration or loss of their properties. Also, as compared to the standard process mentioned above, a filtration step is introduced to remove the additive before the dye solution is added to the dissolution solution. In addition to the standard method listed earlier, details of beryllium analysis by fluorescence are given in several patents and patent applications and all of which can utilize the method of this invention for removing organic impurities that might interfere. These are U.S. Pat. No. 7,129,093 published US patent application 20050280816, published PCT application WO2008130737 and filed U.S. application Ser. No. 12/338, 724 (filed on Dec. 18, 2008). All of these are included herein by reference. PCT patent application Ser. No. 12/338,724 discloses an automation procedure for the robotic preparation of the samples and their manipulation into plates with multiple wells (multiwell plate) and then using a high throughput analyzer that reads all the individual wells for fluorescent signals. It is easy to introduce a filtration step in this automated procedure to filter contents of one multiwell plate to another one to remove the additive before mixing with the optical indicator. The disclosed procedure in this invention for beryllium analysis has also been recently published by Agrawal et al-3.

Figure 5:
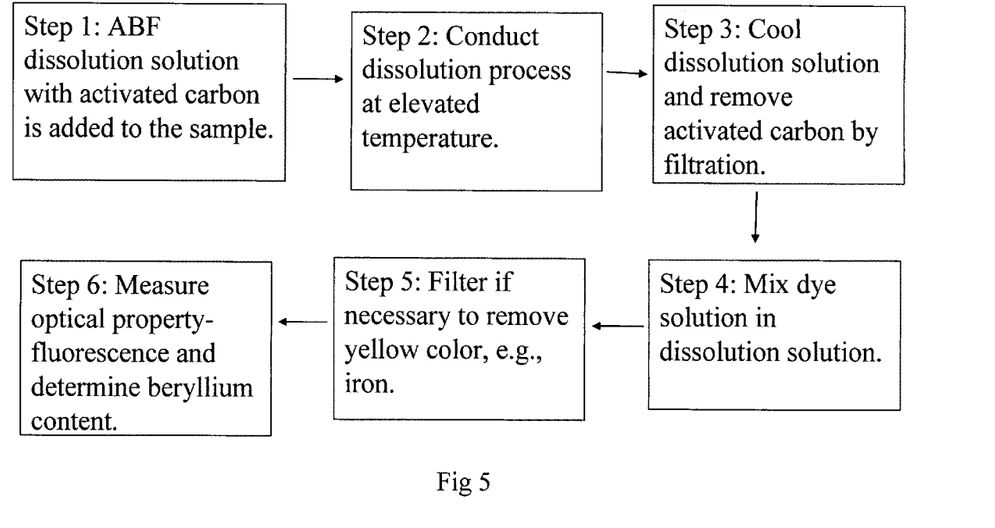
FIG. 5: Shows a schematic diagram of the inventive process.

This invention is explained clearly in FIG. 5 using a preferred embodiment where a standard test method (e.g. see ASTM D7202) is used to analyze beryllium by fluorescence. In Step 1 the sample suspected of having beryllium and perhaps an organic impurity that may interfere with the analysis is added to the dissolution solution (1% ammonium bifluoride in this case) that already has the activated charcoal particles or pellets as additive. The dissolution solution extracts beryllium and any other metal ions present in the sample along with organic impurities that can be solubilized. The additive is to bind or to remove these organic impurities. In Step 2, the dissolution process is carried out for a predetermined time and temperature, and in this case the dissolution is shown to occur at an elevated temperature. In Step 3, the dissolution solution with the sample is cooled (after the completion of the dissolution process) and is filtered to remove the additive which was activated charcoal. Along with the additive any bound organic impurities are removed so that they are unable to interfere with the analysis in the next steps. In Step 4, the fluorescent dye solution is added to the filtered dissolution solution (it should be noted that since the dye is organic, it is added after the additive was removed, otherwise the additive may also bind to this dye). This dye binds with beryllium which results in fluorescence at a specific wavelength. Step 5 filtration is optional, This is needed if other than beryllium, interfering metal ions such as iron and titanium may be present (e.g. see the standard ASTM test method D7202 for details), then these form a precipitate after the dye solution is added and are easily removed by filtration. In Step 6 the optical property, in this case fluorescence is measured to determine the amount of beryllium without any effect from an interfering organic impurity that may have been present in the sample prior to the dissolution step.

Example 1

Interference in Beryllium Reading Caused by Addition of Fluorescent Impurity

To mimic the fluorescent organic impurity Marina Blue succinimidyl ester, was purchased from Invitrogen (Carlsbad, Calif.). The chemical structure of the dye is shown below.

Succinimidyl ester (Marina Blue) was chosen because it exhibits peak excitation wavelength of 365 nm and an emission peak at a wavelength of 460 nm. This is close to the 10-HBQS dye characteristics when it binds to beryllium, i.e., it can be excited at a wavelength of 365 nm and has a peak emission at wavelength of about 475 nm.

Marina Blue was added to a solution of 1 wt % ammonium bifluoride (ABF) until the beryllium reading on the fluorometer at 475 nm was close to that of contamination level of about ~1.34 ppb (ppb is parts per billion). This stock solution was used for all of the subsequent experiments. In addition another 1% ABF solution was prepared with a soluble beryllium contamination level of 0.5 ppb. A third solution with 1% ABF was also made which had both the Marina Blue and beryllium contamination at the above levels. Samples for fluorescence measurements were prepared in cuvettes for emission and excitation spectra by adding 0.1 ml of any of the above ABF solutions to 1.9 ml of detection solution. The detection solution with 10HBQS dye was prepared in water with 63.4 µmol/liter 10-HBQS dye, 2.5 mmol/l EDTA and 50.8 mmol/l of lysine-monohydrochloride. This solution was then titrated with 2.5 mol/liter NaOH solution to adjust the pH at 12.85.

Figure 1:
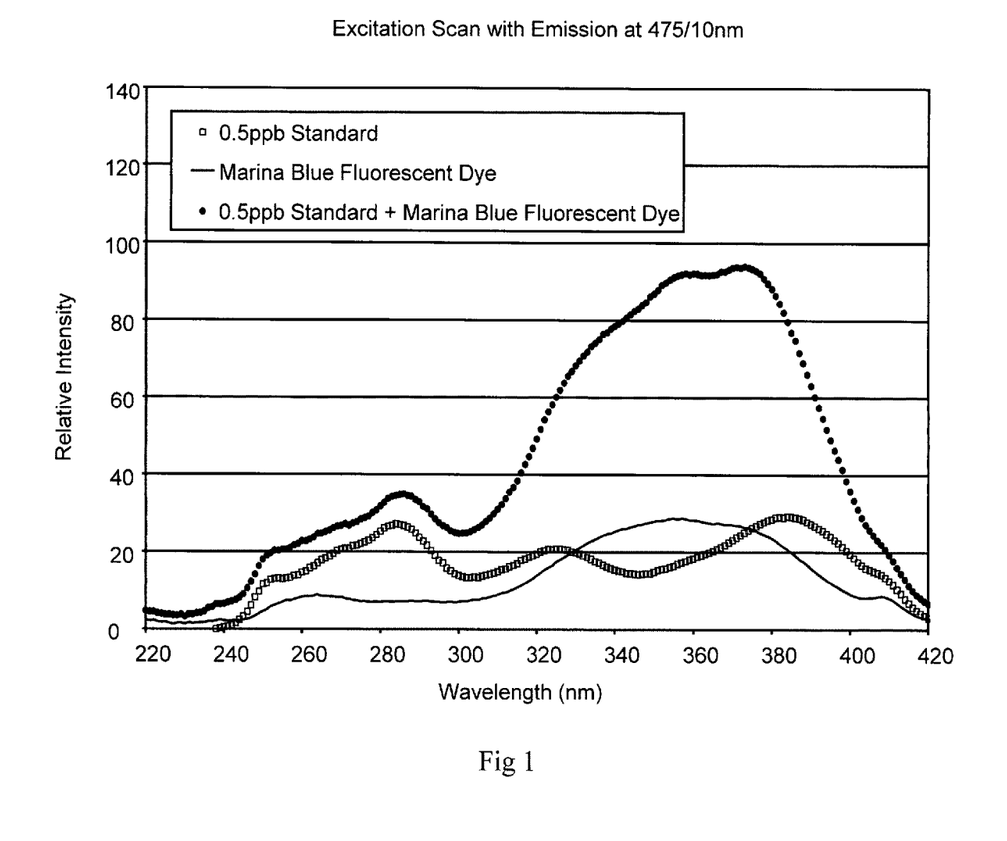
FIG. 1: Excitation spectra of a detection solution with 0.5 ppb beryllium; with no beryllium but with organic impurity; and with 0.5 ppb beryllium and organic impurity.

These samples were analyzed on a Shimadzu fluorescence spectrometer (Model RF 5301PC). FIG. 1 shows the excitation scan with yield emission measured at a wavelength at 475 with a bandwidth of 10 nm. The graphs follow the expected trends. The 0.5 ppb beryllium standard plus the Marina Blue exhibits a more intense signal at 365 nm than the Marina Blue on its own which is more intense than the 0.5 ppb beryllium standard on its own.

Figure 2:
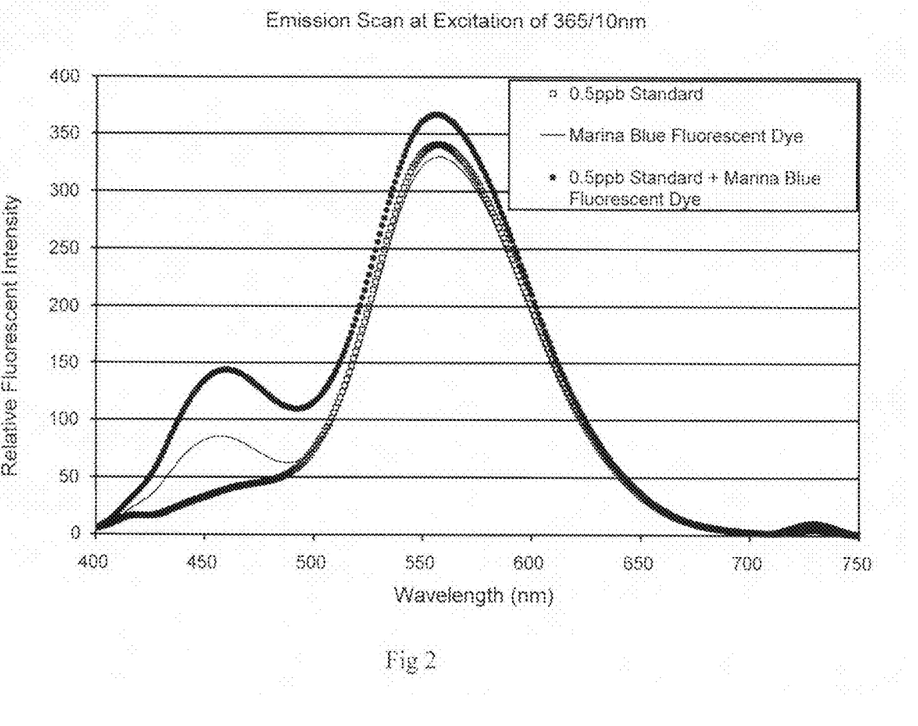
FIG. 2: Emission spectra of a detection solution with 0.5 ppb beryllium; with no beryllium but with organic impurity; and with 0.5 ppb beryllium and organic impurity.

The same trend is seen in FIG. 2, which shows the emission scan with an excitation wavelength of 365 nm and a bandwidth of 10 nm. The signal is most intense for the 0.5 ppb beryllium standard plus the Marina Blue, followed by the Marina Blue on its own and the 0.5 ppb beryllium standard on its own. The information seen in FIGS. 1 and 2 tells us that the Marina Blue is in fact interfering with the beryllium quantification if measured at 475 nm.

Example 2

Removal of Fluorescent Impurity

Figure 3:
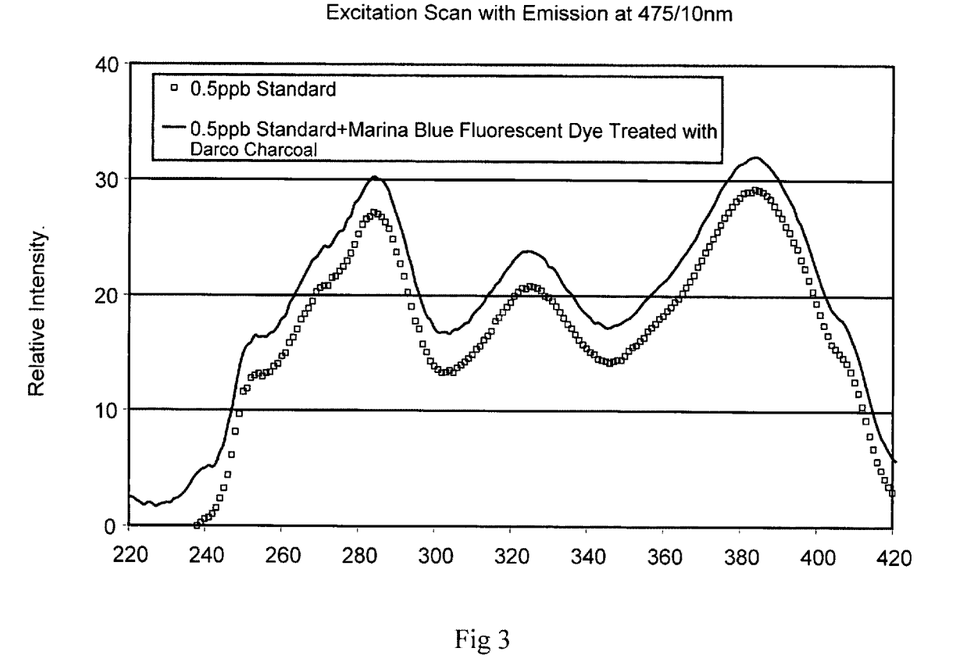
FIG. 3: Excitation spectra of a detection solution with 0.5 ppb beryllium; with 0.5 ppb beryllium and organic impurity where it has been removed by the treatment of this invention.
Figure 4:
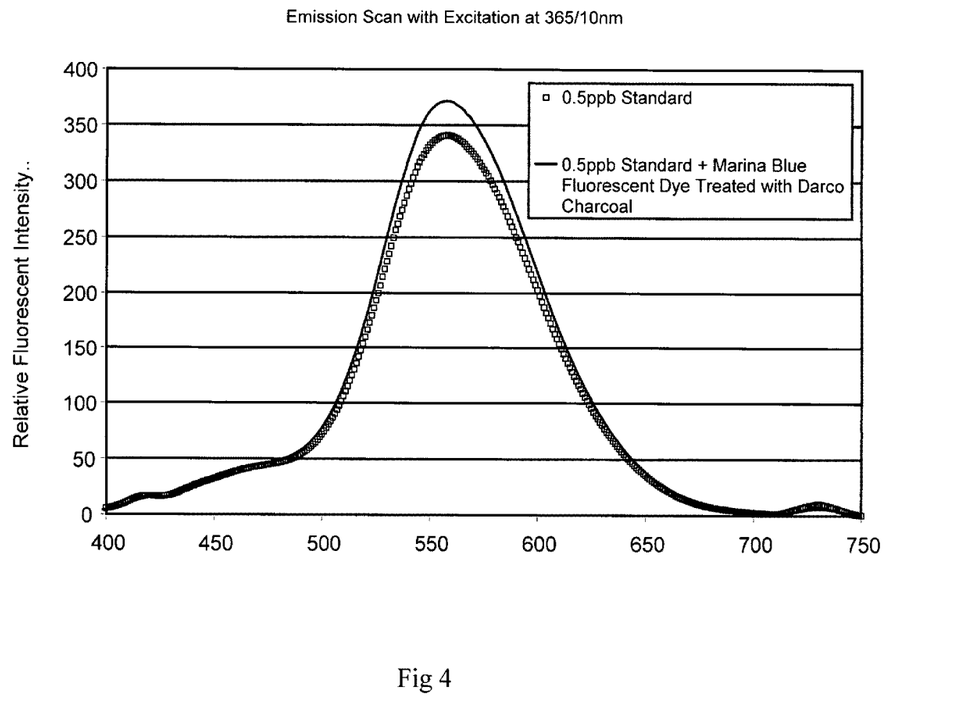
FIG. 4: Emission spectra of a detection solution with 0.5 ppb beryllium; with 0.5 ppb beryllium and organic impurity where it has been removed by the treatment of this invention.

In an effort to eliminate the intense interference signal caused by the Marina Blue, the 0.5 ppb beryllium plus Marina Blue samples were treated with Darco 60 charcoal by adding a small amount (0.001 g to 0.0005 g of activated carbon to each ml of the ABF solution with or without the Marina Blue impurity). The samples were mixed and left to sit at room temperature for 5 minutes. The solutions acquired a black color due to the addition of the charcoal. They were then filtered using 0.2 µm hydrophillic polypropylene (GHP) syringe filters to remove the charcoal additive. The filtered solutions were clear with no observed coloration. 0.1 ml of each was added to 1.9 ml of detection solution. Emission and excitation spectra were then taken as described in Example 1. The results are seen below in FIGS. 3 and 4 where the spectra with the added Marina Blue impurity are very similar to the solution which did not have any Marina blue impurity. This shows that this method was very effective in removing the fluorescent impurity These and other samples as indicated in Table 1 were run on a Modulus fluorometer from Turner Biosystems (Sunnyvale, Calif.), with an LED excitation source at 365 nm and the emission was measured through a filter transmitting between 475 and 485 nm. The fluorometer was calibrated using beryllium standard solutions in a quantity of 0.1 ml with 1.9 ml of the detection solution as described above. The resulting concentration of beryllium in these solutions was 0, 0.5, 2, 10 and 40 ppb. The correlation value of the linear calibration curve was 1. In all examples given in this disclosure similar calibration procedure was used. Several of the samples with or without Marina Blue impurity were treated with the activated charcoal using the procedure described above where these additives were removed before the addition of the detection solution.

TABLE 1

| Sample | Actual ppb reading | Expected beryllium ppb reading |
|---|---|---|
| 0.5 ppb beryllium Standard | 0.5 | 0.5 |
| 0.5 ppb beryllium Standard treated with Darco G-60 activated charcoal | 0.52 | 0.5 |
| Marina Blue | 1.34 | 0 |
| 0.5 ppb beryllium Standard + Marina Blue | 1.76 | 0.5 |
| 0.5 ppb beryllium Standard + Marina Blue treated with Darco G-60 activated charcoal | 0.53 | 0.5 |
| 40 ppb Be Standard treated with Darco G-60 activated charcoal | 39.89 | 40 |

This data shows that untreated samples with fluorescent impurity result in elevated beryllium levels. This data also shows that treating samples with the activated charcoal in the prescribed manner, only removes the fluorescent impurity. The charcoal addition does not cause beryllium readings to change as seen from the samples where no impurity was present but charcoal was added.

In a comparative experiment a measurement solution was made by mixing the detection solution (with fluorescent dye) and a dissolution solution (1.9:0.1 volumetric ratio) where the dissolution solution had both Marina Blue and beryllium. In the final mixed solution, the beryllium concentration was 0.5 ppb, however, due to the presence of Marina Blue this showed an elevated reading for beryllium equivalent to 2.17 ppb on the Modulus fluorometer. Another series of solutions were made where in addition to Marina Blue and beryllium (in the same concentration as above) the dissolution solution also comprised of activated carbon. In one case Darco G-60 activated carbon was used and in the other instead of Darco, acid washed carbon was used. The dissolution solution with carbon was mixed with the dye solution, and after five minutes the carbon additive was filtered out. The beryllium readings on the Modulus fluorometer for these were 0.09 and 0.80 ppb respectively. These were far from the expected beryllium value of 0.5 ppb. This shows that if the additive from the dissolution solution is not removed before adding it to the detection solution the readings for beryllium value are not accurate.

Example 3

Use of Different Type of Activated Charcoal

The same experiments as shown in example 2 using the Modulus fluorometer were repeated using another activated charcoal that was washed with hydrochloric acid (catalogue number C4386 from Aldrich Chemical Co). The results were similar as seen in Table 2. The data shows that treating the 0.5 ppb and the 40 ppb calibration standards, which contain no Marina Blue impurity, with this activated charcoal does not change the beryllium reading. It also shows that when a sample containing the impurity is treated with the activated charcoal the impurity is completely removed.

TABLE 2

| Sample | Actual ppb reading | Expected ppb reading |
|---|---|---|
| 0.5 ppb beryllium Standard | 0.5 | 0.5 |
| 0.5 ppb beryllium Standard treated with activated charcoal (acid washed with HCl) | 0.48 | 0.5 |
| Marina Blue | 1.34 | 0 |
| 0.5 ppb beryllium Standard + Marina Blue | 1.74 | 0.5 |
| 0.5 ppb beryllium Standard treated with activated charcoal, acid washed with HCl | 0.49 | 0.5 |
| 40 ppb beryllium Standard treated with activated charcoal (charcoal acid washed with HCl) | 40.12 | 40 |

Example 4

Use of Oxidizing Additive

In another experiment hydrogen peroxide was used as an oxidizing agent. This was done by adding several drops of peroxide (30% concentration) to 5 ml of dissolution solution with dirty wipe samples with unknown fluorescent impurity and an unknown amount of beryllium and then processed at 85° C. for 30 minutes. Heating also helped in removing the peroxide by decomposition. The resulting solution (0.1 ml) was then added to 1.9 ml detection solution and was read on the Modulus fluorometer. After two hours the samples were then filtered and read again. At this time, the samples treated with hydrogen peroxide gave readings on the Modulus fluorometer that were at about 40% lower than those samples not treated with hydrogen peroxide. Samples without fluorescent impurities did not show any change in the beryllium value after the peroxide treatment.

Example 5

Stability of ABF Dissolution Solution Comprising Charcoal

Darco G-60 activated charcoal (0.5 g) was added to a 500 ml bottle of 1 wt % ABF and was left to stir for 20 minutes. The entire solution was filtered using a 0.2 μm nylon filter. After filtering, another 0.5 g of Darco G-60 activated charcoal was added to the 1 wt % ABF solution. The bottle was shaken by hand and was then left to sit on the lab bench overnight at room temperature. The following day it was noted that the activated charcoal had settled to the bottom of the bottle. Thus this solution needs to be stirred before use.

After sitting on the lab bench for 43 days at room temperature, the pH and the [F−] of the ABF/Darco G-60 solution was checked. The results are shown in the table below.

| Solution | Time left on lab bench at room temperature | pH | [F.−] |
|---|---|---|---|
| 1 wt % ABF with 0.5 g Darco G-60 activated charcoal | None (Initial reading) | 4.718 | 3010 |
| | 43 days | 4.826 | 2940 |

The ABF solution with Darco aged for 43 days, was used to make a sample containing 0.5 ppb beryllium standard and Marina Blue. The solution was filtered to remove the activated carbon and then 0.1 ml of the filtered solution was added to detection solution (1.9 ml) and read on the Modulus fluorometer. A standard sample was made identical to that above using ABF without Darco G-60 activated charcoal. The results are seen in the Table 3. This data shows that the aged solution with activated carbon black performed fine.

TABLE 3

| Sample | Actual ppb reading | Expected beryllium ppb reading |
|---|---|---|
| 0.5 ppb beryllium Standard + Marina Blue 1 wt % ABF | 0.78 | 0.5 |
| 0.5 ppb beryllium Standard + Marina Blue in 1 wt % ABF treated with Darco G-60 activated charcoal after aging for 43 days | 0.47 | 0.5 |

Example 6

Dissolution Under Heated Conditions

Three different activated charcoals were added to three different vials of ABF solutions (1 wt %) containing Marina Blue. The decolorizing charcoal was obtained from Aldrich Chemical Company (product 161551). These solutions were then heated to 90° C. for 30 minutes. After removing from the oven and cooling, these solutions were filtered using 0.2 μm GHP syringe filters and 0.1 ml was added to 1.9 ml of detection solution. The samples were then read on the Modulus fluorometer. The results are seen in Table 4.

TABLE 4

| Sample | ppb reading before dissolution at 90° C. | Actual ppb reading after dissolution at 90° C. | Expected beryllium ppb |
|---|---|---|---|
| Marina Blue, heated to 90 C. for 30 minutes | 1.34 | 1.35 | 0 |
| Marina Blue + Darco G-60 acitvated charcoal, heated to 90 C. for 30 minutes | 1.34 | 0 | 0 |
| Marina Blue + Activated charcoal, acid washed with HCl, heated to 90 C. for 30 minutes | 1.34 | 0 | 0 |
| Marina Blue + Activated charcoal, decolorizing, heated to 90 C. for 30 minutes | 1.34 | 0 | 0 |

The results seen in Table 4 illustrate two important points. First, the data shows that heating the Marina Blue to 90° C. for 30 minutes in 1% ABF solution does diminish fluorescence.

Second, the Marina Blue is completely removed with treatment of all three activated charcoals at an elevated temperature of 90° C.

Example 7

Dissolution Process in 1% ABF Solution with Charcoal, Heated for Long Period Aged 1% ABF solution with Darco charcoal from example 5 and a 1% ABF solutions were used and to both beryllium and Marina Blue were added. The beryllium was added in a quantity to give a value of 0.5 ppb when 0.1 ml of the dissolution solution is mixed with 1.9 ml of the dye solution. These were cooked in closed vials at 90° C. for 22 hours. After the dissolution process, the solutions were filtered to remove carbon from the former solution, and in the latter, filtering was done to keep the preparation processes the same. 1.9 ml of the detection solution was added to 0.1 ml of the filtered dissolution solution and measured on the Modulus fluorometer as described above. The results are shown in Table 5. This shows that if there was no charcoal, the long heat treatment did not remove the increased fluorescence caused by the Marina Blue. Further, the heat treatment with charcoal was also effective in removing the organic impurity as were the room temperature treatments.

TABLE 5

| Sample | Actual ppb reading | Expected ppb beryllium reading |
|---|---|---|
| 0.5 ppb Standard + Marina Blue, heated to 90° C. for 22 hours | 1.35 | 0.5 |
| 0.5 ppb Standard + Marina Blue + Darco G-60 acivated charcoal that had been sitting for 43 days at room temp. in 1 wt % ABF, heated to 90° C. for 22 hours | 0.54 | 0.5 |

Example 8

Dissolution Using 3% ABF Aqueous Solution for 40 Hrs at 90° C. with and Without Charcoal 3 wt % ABF solutions in water have been shown to be an effective dissolution medium for soils, rocks, sediments and flyash when treated for 40 hours at 90° C. as required in ASTM test method D7458. In this example we wanted to test if the addition of charcoal is still an effective method as described in previous examples so that it may be used for the dissolution of the above materials. Darco G-60 activated charcoal was added to a 3 wt % ABF solution. To another similar solution, acid washed charcoal (with HCl) was added rather than Darco. Further, Marina Blue and beryllium were added and the solutions were heated to 90° C. for 40 hours. After heating, the solutions were cooled to room temperature and filtered using a 0.2 μm GHP syringe filter. Samples were then made by taking 0.1 ml of the filtered solution and mixing it with 1.9 ml of detection solution. These samples were then read on the Modulus fluorometer. The results are seen in Table 6 below. First if there was no charcoal the results showed elevated beryllium value due to the interference from the organic impurity (Marina Blue). When charcoal was added then both of these were effective in removing the organic impurity. The high ABF concentration and the long processing time at 90° C. did not cause any problems with the added charcoal.

TABLE 6

| Sample | Actual ppb reading | Expected ppb beryllium reading |
|---|---|---|
| 0.5 ppb Standard + Marina Blue in 3 wt % ABF, heated to 90° C. for 40 hours | 0.98 | 0.5 |
| 0.5 ppb Standard + Marina Blue + Darco G-60 activated charcoal in 3 wt % ABF, heated to 90° C. for 40 hours | 0.45 | 0.5 |
| 0.5 ppb Standard + Marina Blue + activated charcoal, acid washed in HCl in 3 wt % ABF, heated to 90° C. for 40 hours | 0.51 | 0.5 |

While this invention has been described as having preferred sequences, ranges, steps, materials, structures, features, and/or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

What is claimed is:

1. An optical method of determining the presence or amount of metal or a metal compound in a sample with organic impurities, where the method comprises:
    (a) dissolving the said metal or its compound in a liquid medium or obtaining a sample pre-dissolved in a liquid medium ,
    (b) subjecting the said liquid medium to an additive to bind or react with the organic impurity
    (c) removing the additive
    (d) mixing the said liquid medium with a indicator solution to form a detection solution
    (e) measuring the detection solution by an optical method.

2. An optical method as in claim 1, wherein the metal is beryllium, lead and hexavalent chromium.

3. An optical method as in claim 1, wherein the liquid medium is ammonium bifluoride.

4. An optical method as in claim 1, where in the indicator is 10-hydroxybenzo [h] quinoline-7-sulfonate.

5. An optical method as in claim 1, wherein the optical method is fluorescence.

6. An optical method as in claim 1, wherein the additive is selected from one of a reducing agent, oxidizing agent and activated carbon.

7. An optical method of determining the presence or amount of metal or a metal compound in a sample with organic impurities, where the method comprises:
    (a) dissolving the said metal or its compound in a liquid medium wherein the said liquid medium comprises of an additive to bind or react with the organic impurity
    (b) removing the additive
    (c) mixing the said liquid medium with a indicator solution to form a detection solution
    (d) measuring the detection solution by an optical method.

8. An optical method as in claim 7, wherein the metal is beryllium, lead and hexavalent chromium.

9. An optical method as in claim 7, wherein the liquid medium is ammonium bifluoride.

10. An optical method as in claim 7, where in the indicator is 10-hydroxybenzo [h] quinoline-7-sulfonate.

11. An optical method as in claim 7, wherein the optical method is fluorescence.

12. An optical method as in claim 7, wherein the additive is selected from one of a reducing agent, oxidizing agent and activated carbon.

13. An optical method of determining the presence or amount of beryllium or a beryllium compound in a sample with organic impurities, where the method comprises:

(a) dissolving the beryllium or its compound in a ammonium bifluoride aqueous solution wherein the said ammonium bifluoride solution comprises additive which is activated carbon that binds or reacts with the organic impurities, (c) removing the additive from the ammonium bifluoride solution (d) mixing the ammonium bifluoride solution with an indicator solution comprising 10-hydroxybenzo[h]quinoline-7-sulfonate to form the detection solution (e) measuring fluorescence from the detection solution to quantify beryllium.

* * * * *